United States Patent [19]

Machida

[11] Patent Number: 5,587,508
[45] Date of Patent: Dec. 24, 1996

[54] PROCESS FOR PRODUCING 2,6-NAPHTHALENEDICARBOXYLIC ACID AND ESTER THEREOF

[75] Inventor: Hiroshi Machida, Okayama-ken, Japan

[73] Assignee: Mitsubishi Gas Chemical Company, Inc., Tokyo, Japan

[21] Appl. No.: 580,974

[22] Filed: Jan. 3, 1996

[30] Foreign Application Priority Data

Jan. 11, 1995 [JP] Japan .................................. 7-002708

[51] Int. Cl.$^6$ .......................... C07C 67/00; C07C 51/215
[52] U.S. Cl. ............................ 560/77; 562/414; 562/416
[58] Field of Search ........................... 560/77; 562/414, 562/416

[56] References Cited

U.S. PATENT DOCUMENTS

| | | | |
|---|---|---|---|
| 3,487,108 | 12/1969 | Chibnik et al. | 260/524 |
| 3,856,855 | 12/1974 | Yamashita et al. | 260/524 R |
| 4,764,638 | 8/1988 | Feld | 562/416 |
| 5,183,933 | 2/1993 | Harper et al. | 562/414 |
| 5,442,103 | 8/1995 | Iwane et al. | 562/416 |
| 5,523,473 | 6/1996 | Saitou et al. | 562/416 |

FOREIGN PATENT DOCUMENTS

| | | |
|---|---|---|
| 121255 | of 1975 | Japan . |
| 35697 | of 1982 | Japan . |
| 65143 | of 1994 | Japan . |
| 727989 | 4/1955 | United Kingdom . |

*Primary Examiner*—Paul J. Killos
*Assistant Examiner*—Barbara S. Frazier
*Attorney, Agent, or Firm*—Roylance, Abrams, Berdo & Goodman, L.L.P.

[57] ABSTRACT

A process for producing 2,6-naphthalenedicarboxylic acid (NDCA) is disclosed. This process comprises oxidizing a 2,6-dialkylnaphthalene with a gas containing molecular oxygen in a solvent containing a lower aliphatic carboxylic acid in the presence of a catalyst comprising heavy metal compounds and a bromine compound, and is characterized in that an ester mixture containing dimethyl 2,6-naphthalenedicarboxylate (NDCM) is added to the oxidation reaction. The low boiling distillate, the high boiling still residue, and the residue of the mother liquor after recrystallization, occurring during purification of the crude NDCM, are also used as additives to the oxidation reaction. According to the present invention, NDCA with large particle size and bulk density can be obtained. Therefore, solid-liquid separation of the crystals, drying of the separated crystals and transportation of the dried crystals are made easier.

4 Claims, No Drawings

PROCESS FOR PRODUCING 2,6-NAPHTHALENEDICARBOXYLIC ACID AND ESTER THEREOF

FIELD OF THE INVENTION

This invention relates to a process for producing 2,6-naphthalenedicarboxylic acid (hereinafter referred to as NDCA) which is useful as a raw material for high functional polyesters, and dimethyl 2,6-naphthalenedicarboxylate (hereinafter referred to as NDCM).

DESCRIPTION OF THE PRIOR ART

Known methods for producing NDCA have been to oxidize 2,6-dialkylnaphthalenes in solvents containing lower aliphatic carboxylic acids by use of catalysts containing cobalt, manganese and bromine (Japanese Patent Publication No. 2666/1959 and U.S. Pat. No. 3,856,855).

Since NDCA has very low solubility in solvents, NDCA formed by oxidation generally occurs as crystals precipitated in the reactor. According to the reaction methods and reaction conditions described in the above patent publications, the particle diameters of the NDCA crystals precipitated are very small. Thus, the problems are posed that when the crystals and the solvent are separated from each other by commercially customary methods such as centrifugal sedimentation, centrifugal filtration or vacuum filtration, the crystals migrate in large amounts into the mother liquor, the filter cloth is clogged, and the liquid content of the cake separated is very high. This high liquid content of the cake presents the problems that the crystals are accompanied by large amounts of the oxidation catalyst, and that much energy is required for removing the solvent in drying the crystals. The NDCA crystals after drying are small in bulk density and poor in flowability, thus involving the problems of necessity of the large reservoir or the like for the crystals, and huge costs for preventing the bridging of and blocking by the crystals during transportation.

As a way of increasing the sizes of the NDCA crystals and improving their properties such as separability, Japanese Patent Publication (Kokai) No. 121255/1975 discloses a method of maintaining a slurry after reaction at a temperature of 20° to 100° C. for 4 hours or more, thereby agglomerating the crystals. Japanese Patent Publication (Kokai) No. 65143/1944 states that oxidation performed at a temperature in a specific range (180° to 220°) makes the particle diameter of NDCA large.

Furthermore, NDCA produced by oxidation contains organic impurities such as trimellitic acid and 6-formyl-2-naphthoic acid, and heavy metals such as cobalt and manganese from the oxidation catalyst. Unless these substances are removed for purification, the NDCA is not suitable for use as a starting material for a high functional polymer. As stated earlier, however, NDCA has low solubility in solvents, and decomposes at its melting point. Thus, it is difficult to purify NDCA as such. Under these circumstances, Japanese Patent Publication Nos. 35697/1982 and 9697/1971 describe methods which comprise esterifying NDCA with methanol to form NDCM, and then distilling or recrystallizing it for purification.

The impurity concentrates occurring during this purification step (e.g., low boiling distillate and high boiling bottom by distillation, and mother liquor separated after recrystallization) contain considerably amounts of NDCM. Their handling as wastes would decreases the yield of NDCM in the entire process.

As described above, NDCA formed by oxidation comprises precipitated crystals having very small particle diameters, making it difficult to separate the crystals from the solvent. In addition, the NDCA crystals are small in build density and poor in flowability, thus lowering the volume efficiency of the crystal reservoir or the like, and requiring huge costs for transportation of the crystals.

Our studies of the aforementioned Japanese Patent Publication (Kokai) Nos. 121255/1975 and 65143/1944 describing methods for increasing the particle diameters of the NDCA crystals have obtained the following findings: The resulting NDCA crystals are plant-like to strip-like crystals and crystals comprising their agglomerates. These crystals are crushed very easily, and become fine during the travel of the slurry by a pump or the like. Thus, improvements in their separability by, say, decreasing the migration of the crystals into the mother liquor and the liquid content of the cake are not necessarily sufficient. Moreover, little improvement is achieved in the bulk density or flowability of the dried crystals. Consequently, the problems with the storage and transportation of the NDCA crystals remain unsolved.

SUMMARY OF THE INVENTION

Therefore, an object of the present invention is to provide a method of producing NDCA commercially advantageously by increasing the particle diameters and bulk density of NDCA crystals, formed by oxidation of a dialkylnaphthalene, to facilitate solid-liquid separation of the crystals, drying of the separated crystals, and transportation of the dried crystals.

We conducted extensive studies to solve the aforementioned problems with the production of NDCA. As a result, we have found that by adding an ester mixture containing NDCM during oxidation of a dialkylnaphthalene with an oxygen-containing gas, crystals of NDCA formed by the reaction grow to large spheres, and their bulk density also increases, thus facilitating solid-liquid separation of the crystals, drying of the separated crystals, and powdery transportation of the dried crystals; and that by using an ester mixture, obtained at a step of purifying crude NDCM, as the NDCM-containing ester mixture, the yield of the NDCM production process is increased, and NDCM is produced favorably. These findings have led us to accomplish the present invention.

That is, the present invention is a process for producing NDCA, which comprises oxidizing a 2,6-dialkylnaphthalene with a gas containing molecular oxygen in a solvent containing a lower aliphatic carboxylic acid in the presence of a catalyst comprising heavy metal compounds and a bromine compound, wherein an ester mixture containing NDCM is added to the oxidation reaction; and a process for producing NDCM which comprises oxidizing a 2,6-dialkylnaphthalene with a gas containing molecular oxygen to produce NDCA, and purifying a reaction product obtained by the reaction between the NDCA and methanol, wherein an ester mixture containing NDCM obtained by the purification step is added to the oxidation reaction.

DETAILED DESCRIPTION OF THE INVENTION

Examples of the 2,6-dialkylnaphthalene used as the starting material for the oxidation reaction in the present invention include 2,6-dimethylnaphthalene (hereinafter referred to as DMN), 2,6-diethylnaphthalene and 2,6-diisopropylnathphalene. Examples of the lower aliphatic carboxylic acid used as the solvent are formic acid, acetic acid, propionic acid, butyric acid, and mixtures of these acids. Of them, acetic acid is the most preferred. The solvent may contain water, but its content is 30% by weight or less. The amount of the solvent used is 1 to 20 times, preferably, 3 to 10 times, the weight of the dialkylnaphthalene as the starting material for oxidation.

The oxidation catalyst used in the present invention is a cobalt compound, a manganese compound and a bromine compound. If desired, a compound of a heavy metal such as iron, cerium or nickel may be added thereto. Examples of the cobalt, manganese and other heavy metal compounds are organic acid salts, hydroxides, halides, and carbonates. Acetates and bromides, in particular, are preferred. The bromine compounds may be any ones which dissolve in the reaction system to generate bromine ions. Their examples are inorganic bromides such as hydrogen bromide, sodium bromide and cobalt bromide, as well as organic bromides such as bromoacetic acid. Preferred examples are hydrogen bromide, cobalt bromide and manganese bromide.

The oxidation catalyst, if it contains a heavy metal component comprising cobalt and manganese, is added in such an amount that the total amount of the cobalt and manganese is at an atomic ratio of 0.02–0.5, preferably, 0.05–0.3, to the dialkylnaphthalene as the starting material for oxidation. Bromine is added at an atomic ratio of 0.01–0.3, preferably, 0.02–0.15, to the starting material for oxidation. If the amount of the catalyst is less than this range, the yield of NDCA by the reaction will decrease. Its amount in excess of that range will not increase the yield.

The gas containing molecular oxygen used in the present invention is oxygen gas, or a mixture of oxygen and an inert gas such as nitrogen or argon, but air is the most preferred gas. The mode of the oxidation reaction may be batchwise, semi-batchwise, or continuous.

The reaction temperature for the oxidation reaction in the present invention is 190° to 240° C., and the reaction pressure is 5 to 40 kg/cm$^2$ G, preferably, 10 to 30 kg/cm$^2$ G. The oxygen partial pressure in the reaction is preferably 0.005 kg/cm$^2$ (absolute pressure) or more. The oxygen pressure lower than this would increase the reaction intermediate, and decrease the yield of NDCA.

Examples of the NDCM-containing ester mixture added to the oxidation reaction in the present invention include crude NDCM containing impurities which has been obtained by esterifying crude NDCA with methanol; high purity NDCM obtained by purifying the crude NDCM by distillation or recrystallization; low boiling distillate and high boiling bottom (still residue) occurring during distillation of the crude NDCM; and residue obtained by evaporating the solvent from the mother liquor separated after purification by recrystallization (called the recrystallization mother liquor residue). The crude NDCM and the high purity NDCM may be used as additives if improvements in crystal properties (particle diameter, bulk density, and flowability) are aimed at. If it is also attempted to increase the NDCM yield of the entire process, there is need to use the still residue, the low boiling distillate, the recrystallization mother liquor residue, or a mixture of any of these.

The larger the amount of the ester mixture is, the larger the particle diameters and bulk density of the NDCA crystals become, and the higher effect of improving their properties is achieved. However, the ester mixture forms a lower aliphatic carboxylic acid ester by ester interchange with the lower aliphatic carboxylic acid as the solvent in the oxidation reactor, thereby causing a loss of the solvent. Thus, adding the ester mixture in a larger amount than required is not preferred. The amount of the ester mixture added is 2 to 30% by weight, preferably, 5 to 20% by weight, based on the dialkylnaphthalene as the starting material for oxidation.

The NDCA crystals formed by the oxidation reaction are separated from the solvent by a solid-liquid separator. By type, the separator is a centrifugal precipitator, a centrifugal filter, or a vacuum filter. The minimum particle diameter of crystals that can be separated by any of these separators is usually 5 μm with a decanter type centrifugal precipitator, or 10 to 20 μm with a centrifugal filter or a vacuum filter. The NDCA crystals obtained by the present invention are of particle diameters suitable for any type of separator cited above.

The NDCA crystals after separation are deprived of the solvent by a dryer, and then used as the starting material for the esterification reaction. Before drying, the crystals may be mixed with water and/or a solvent comprising a lower aliphatic carboxylic acid to turn them into a slurry again, whereafter the slurry may be subjected again to solid-liquid separation. This procedure can remove the impurities and the oxidation catalyst contained in the crystals, raising the purity of NDCA. In such crystal washing and drying, the lower the liquid content of the solid-liquid separation case is, the higher the re-slurry/washing effect becomes, and the greater drying capacity and the more energy saving are achieved for the dryer. Moreover, large bulk density of the crystals makes the volume efficiency of the dryer higher, permitting treatment with a smaller dryer. Since the present invention gives crystals with a low liquid content and a large bulk specific gravity, the reslurry/washing and drying of the crystals can be performed advantageously.

In the commercial production of NDCM, the crude NDCA crystals after drying are transported in powdery state to a subsequent esterification step mechanically or pneumatically. In this powder-state transportation, larger bulk density and high flowability give a greater saving of costs for the transportation equipment. Generally, the flowability of powder is expressed by such measures as the degree of compaction (the difference between the bulk density of the powder charged densely and that of the powder charged sparsely) and the angle of repose. In the present invention, these measures are low in value, meaning that highly flowable crystals are obtained.

The esterification reaction between NDCA and methanol is performed by a known method. The reaction temperature is 100° to 320° C., and the reaction pressure is 2 to 200 kg/cm$^2$ G. The catalyst for esterification is sulfuric acid or a molybdenum compound such as molybdenum trioxide. However, the reaction can be performed noncatalytically, if an elevated temperature of 240° C. is employed.

The mode of the esterification may be batchwise, semi-batchwise or continuous. As mentioned previously, NDCA has low solubility in solvents, and decomposes at its melting point. Thus, when the reaction is carried out in a semi-batchwise or continuous manner, NDCA is dispersed in a solvent, and continuously fed in a slurry state to the reactor. A preferred solvent is methanol or molten NDCM.

Crude NDCM formed by the esterification reaction is purified by a method such as distillation or recrystallization to obtain high purity NDCM.

The distillation of NDCM is performed at a reduced pressure of 1 to 50 mmHg and a temperature of 210° to 280° C. The solvent used for recrystallization is, for example, methanol, an aromatic hydrocarbon such as xylene, or chlorobenzene. Methanol and xylene, in particular, are preferred. The preferred amount of the solvent used is 2 to 10 times the weight of NDCM. Crystals precipitated by recrystallization can be separated from the mother liquor by a customary method such as centrifugal precipitation, centrifugal filtration or vacuum filtration.

The concentrates of the impure components occurring at the purification step (e.g. low boiling distillate and high boiling bottom occurring during distillation, and residue obtained by evaporating the solvent from the mother liquor separated after recrystallization) contain NDCM. Thus, they can be used as additives for the oxidation reaction in the present invention.

EXAMPLES

The present invention will be described in detail by Examples, which do not limit the invention.

The yield of NDCA, particle diameters of crystals, bulk density, and degree of compaction shown in the Examples and Control Runs will be defined and measured as follows:

(1) Yield of NDCA

In the Examples in which the ester mixture was added, NDCM, NDCA and naphthalenedicarboxylic acid monomethyl ester contained in the additive (these three components are collectively called the NDCA composition) were subtracted in calculating the yield, which was expressed as the molar ratio:

Yield of NDCA (%)=[(content of NDCA composition in the product)−(content of NDCA composition in the additive)]/(feed of DMN)×100

(2) Particle diameters of crystals

The 50% value of the cumulative distribution of the particle diameters determined using a laser diffraction type particle diameter distribution measuring device is indicated as the average particle diameter of the crystals.

(3) Bulk density at sparse packing

The crystals were sieved, packed into a container of a fixed volume, and measured for the bulk density.

(4) Bulk density at dense packing

The above container sparsely packed with the crystals was given tapping vibrations so as to create a dense packing, and the bulk density was measured.

(5) Degree of compaction

Degree of compaction (%)=[(Bulk density at dense packing)−(Bulk density at sparse packing)]/(Bulk density at dense packing)×100

Control Run 1

(1) Oxidation reaction

32 Grams of water, 6.4 g of cobalt acetate (tetrahydrate), 53.5 g of manganese acetate (tetrahydrate) and 19.4 g of hydrogen bromide (47% aqueous solution) were mixed with 2,889 g of acetic acid, and the mixture was dissolved to prepare a catalyst solution. Then, 1,200 g of this catalyst solution was charged into a 5-liter titanium autoclave (reactor) equipped with a stirrer, a reflux condenser and a starting material feeding pump. The remaining 1,800 g of the catalyst solution was mixed with 300 g of 2,6-dimethylnaphthalene (DMN), and charged into a starting material feed tank, where the mixture was heated to dissolve DMN, preparing a stock solution.

The reaction system was heated at a temperature of 200° C. with stirring, with the pressure inside it being adjusted to 18 kg/cm$^2$ G with nitrogen. After the temperature and the pressure became stable, the stock solution and compressed air were fed to the reactor to initiate oxidation. With the flow rate of the fed air being adjusted to keep the oxygen concentration in the waste gas at 2% by volume, the stock solution was fed continuously over 1 hour. The oxygen partial pressure inside the reactor at this time was 0.12 kg/cm$^2$ (absolute pressure). After supply of the stock solution was completed, the feed of air was continued for 9 minutes.

Upon completion of the reaction, the autoclave was cooled to room temperature. The reaction product was withdrawn, and suction filtered through a glass filter to separate the crystals formed. They were rinsed in 800 g of acetic acid containing 20% by weight of water. The filter cake was measured for weight, and then dried by a dryer to obtain 408.2 g of crude NDCA crystals. The liquid content of the cake calculated from the loss on drying was 59.9% by weight (based on the wet weight). The purity of NDCA in the dry crystals was 96.8% by weight, and the yield of NDCA based on the DMN fed was 95.2 mol %.

The resulting dry crystals had an average particle diameter of 17 μm, a bulk density at sparse packing of 0.22 g/cm$^3$, and a bulk density at dense packing of 0.36 g/cm$^3$. These parameters meant a degree of compaction of 39%. The angle of repose was 65 degrees.

(2) Esterification reaction

A 5-liter titanium autoclave equipped with a stirrer and a reflux condenser was charged with 400 g of the crude NDCA crystals obtained by the oxidation reaction, 2,400 g of methanol and 40 g of concentrated sulfuric acid. After the inside of the autoclave was purged with nitrogen, the reaction system was heated, and the esterification reaction was performed at a temperature of 130° C. and a pressure of 12 kg/cm$^2$ G for 1.5 hours. Upon completion of the reaction, the autoclave was cooled to room temperature. The reaction product was withdrawn, and suction filtered through a glass filter to separate the crystals formed. The cake separated was rinsed in 1,200 g of methanol, and then dried. The weight of the resulting crude NDCM crystals was 418.8 g. The purity of NDCM in the crystals was 97.2% by weight, and the yield of NDCM by the esterification reaction was 93.1 mol %.

(3) Purification of ester 400 g of the crude NDCM obtained by the above esterification reaction was purified by batchwise distillation at a reduced pressure of 16 mmHg to obtain 357.2 g of the distillate with an NDCM purity of 99.9% by weight. The amount of the high boiling still residue was 34.8 g, and it consisted of 31.2% by weight of NDCM, 54.9% by weight of naphthalenedicarboxylic acid monoester, 2.4% by weight of NDCA, and 11.5% by weight of other high boiling substances.

Then, 350 g of the distillate was heated in 2,100 g of m-xylene under reflux for 1 hour at atmospheric pressure to dissolve it. Then, the solution was left to cool to room temperature to precipitate crystals. This slurry was suction filtered through a glass filter to separate the crystals. The crystals after drying weighed 335.3 g, and gave purified NDCM having an NDCM purity of more than 99.9% by weight. The mother liquor was heated to distill off the solvent, whereby 14.1 g of the residue with an NDCM content of 98% by weight was obtained.

The yield of pure NDCM based on the oxidation material (DMN) after all steps, oxidation, esterification and purification, was 77.8 mol %.

Example 1

Oxidation was performed under the same conditions and by the same procedure as in Control Run 1, except that 60 g of the purified NDCM obtained in Control Run 1 (weight ratio to DMN: 20%) was charged into the reactor along with the catalyst solution.

The resulting product was separated in crystal form by the same procedure as in Control Run 1 to obtain 438 g of crude NDCA crystals. The content of the NDCA composition, the liquid content in the cake, the average particle diameter, the bulk density, the degree of compaction, and the angle of repose that the resulting crystals had are shown in Table 1 together with the yield of NDCA by the oxidation.

Example 2

(1) Oxidation reaction

Oxidation was performed under the same conditions and by the same procedure as in Control Run 1, except that 30 g of the still residue obtained in Control Run 1 (weight ratio to DMN: 10%) was charged into the reactor along with the catalyst solution.

The resulting product was separated in crystal form by the same procedure as in Control Run 1 to obtain 436 g of crude NDCA crystals. The content of the NDCA composition, the liquid content in the cake, the average particle diameter, the bulk density, the degree of compaction, and the angle of repose that the resulting crystals had are shown in Table 1 together with the yield of NDCA by the oxidation.

(2) Esterification reaction

Using 400 g of the crude NDCA obtained in the above oxidation reaction, esterification was performed under the same conditions and by the same procedure as in Control Run 1.

The weight of the NDCM crystals obtained was 414.7 g, the purity of NDCM in the crystals was 97.9% by weight, and the yield of NDCM by the esterification was 93.2 mol %.

(3) Purification of ester 400 g of the crude NDCM obtained by the above esterification reaction was distilled under the same conditions and by the same procedure as in Control Run 1 to obtain 356.4 g of the distillate with an NDCM purity of 99.8% by weight. The amount of the still residue was 35.2 g, and it consisted of 49.5% by weight of NDCM, 34.5% by weight of naphthalenedicarboxylic acid monoester, 1.8% by weight of NDCA, and 14.2% by weight of other high boiling substances.

Then, 350 g of the distillate was recrystallized for purification under the same conditions and by the same procedure as in Control Run 1. The crystals after drying weighed 334.3 g, and gave purified NDCM having a 2,6-NDCM purity of more than 99.9% by weight. The mother liquor was heated to distill off the solvent, whereby 15.5 g of the residue with an NDCM content of 95.7% by weight was obtained.

The yield of NDCM based on the oxidation material (DMN) after all steps, oxidation, esterification and purification, was 82.0 mol %.

Example 3

Oxidation was performed under the same conditions and by the same procedure as in Control Run 1, except that 30 g of the still residue and 15 g of the recrystallization mother liquor residue (the weight ratio of the total amount of both to DMN: 15%) obtained in Example 2 were charged into the reactor along with the catalyst solution.

The resulting product was separated in crystal form by the same procedure as in Control Run 1 to obtain 428 g of crude NDCA crystals. The content of the NDCA composition, the liquid content in the cake, the average particle diameter, the bulk density, the degree of compaction, and the angle of repose that the resulting crystals had are shown in Table 1 together with the yield of NDCA by the oxidation.

TABLE 1

| | Cont. Run 1 | Ex. 1 | Ex. 2 | Ex. 3 |
| --- | --- | --- | --- | --- |
| Content of NDCA composition (wt. %) | 96.8 | 97.9 | 96.4 | 98.1 |
| Yield of NDCA (mol %) | 95.2 | 90.5 | 95.3 | 92.6 |
| Liquid content in cake (wt. %) | 59.9 | 38.3 | 34.2 | 33.8 |
| Average particle diameter ($\mu$m) | 17 | 24 | 28 | 36 |
| Bulk density at sparse packing (g/cm$^3$) | 0.22 | 0.52 | 0.56 | 0.63 |
| Bulk density at dense packing (g/cm$^3$) | 0.36 | 0.76 | 0.76 | 0.82 |
| Degree of compaction (%) | 39 | 32 | 26 | 23 |
| Angle of repose (degrees) | 65 | 50 | 45 | 42 |

Control Run 2

(1) Oxidation reaction

Oxidation and crystal separation were performed under the same conditions and by the same procedure as in Control Run 1 to obtain 406 g of crude NDCA crystals. The content of the NDCA composition, the liquid content in the cake, the average particle diameter, the bulk density, the degree of compaction, and the angle of repose that the resulting crystals had are shown in Table 2 together with the yield of NDCA by the oxidation.

The concentrations of the heavy metals in the crude NDCA crystals were 0.022% by weight for Co and 0.26% by weight for Mn.

(2) Esterification reaction

A 2-liter autoclave equipped with a stirrer was charged with 360 g of the crude NDCA crystals obtained in the above oxidation reaction and 500 g of methanol. After the inside of the autoclave was purged with nitrogen, the reaction system was heated, and held for 0.5 hour at a temperature of 260° C. and a pressure of about 80 kg/cm$^2$ G. Then, part of the methanol vapor in the gas phase of the reactor was withdrawn to adjust the pressure to 50 kg/cm$^2$ G. With methanol being continuously fed at a flow rate of 830 g/hr to the liquid phase of the reactor, and methanol vapor being withdrawn from the gas phase, the esterification reaction was performed for 2 hours at a temperature of 260° C. and a pressure of 50 kg/cm$^2$ G. Upon completion of the reaction, methanol vapor was taken out to lower the inside pressure of the reactor, and crude NDCM formed was withdrawn in molten state. The weight of the resulting crude NDCM was 389 g, and its NDCM content was 93.4% by weight. The yield of NDCM by the esterification was 95.8 mol %, including the NDCM withdrawn to the outside of the reactor as an incidental to the methanol vapor during the reaction.

(3) Ester purification

360 Grams of the crude NDCM obtained by the above esterification reaction was distilled under the same conditions and by the same procedure as in Control Run 1 to obtain 312.9 g of the distillate with an NDCM purity of 98.8% by weight. The amount of the still residue was 39.4 g, and it consisted of 54.7% by weight of NDCM, 17.4% by weight of naphthalenedicarboxylic acid monoester, 9.2% by weight of NDCA, 2.2% by weight of heavy metals (Co= 0.18% by weight, Mn=2.04% by weight), and 16.2% by weight of other high boiling substances.

Then, 300 g of the distillate was recrystallized for purification under the same conditions and by the same procedure as in Control Run 1. The crystals after drying weighed 284.8 g, and gave purified NDCM having an NDCM purity of more than 99.9% by weight.

The yield of NDCM based on the oxidation material (DMN) after all steps, oxidation, esterification and purification, was 80.3 mol %.

Example 4

(1) Oxidation reaction

Oxidation was performed under the same conditions and by the same procedure as in Control Run 1, except that 30 g of the still residue (weight ratio to DMN: 10%) obtained in Control Run 2 was charged into the reactor along with the catalyst solution. The catalyst solution was prepared so that the catalyst concentration was made equal to that in Control Run 1 by decreasing the amounts of the Co and Mn compounds used by the weights of the Co and Mn contained in the still residue added.

The resulting product was separated in crystal form by the same procedure as in Control Run 1 to obtain 423 g of crude NDCA crystals. The content of the NDCA composition, the liquid content in the cake, the average particle diameter, the bulk density, the degree of compaction, and the angle of repose that the resulting crystals had are shown in Table 2 together with the yield of NDCA by the oxidation.

The concentrations of the heavy metals in the crude NDCA crystals were 0.014% by weight for Co and 0.15% by weight for Mn. Because of the effect of decreasing the liquid content of the cake separated, the crude NDCA crystals of Example 4 have lower heavy metal concentrations than do those of Control Run 2.

(2) Esterification reaction

Using 360 g of the crude NDCA obtained by the above oxidation reaction, esterification was performed under the same conditions and by the same procedure as in Control Run 2.

The weight of the resulting crude NDCM was 387 g, and its NDCM content was 94.1% by weight. The yield of NDCM by the esterification was 95.3 mol %, including the NDCM withdrawn to the outside of the reactor as an incidental to the methanol vapor during the reaction.

(3) Purification of ester

360 Grams of the crude NDCM obtained by the above esterification reaction was distilled under the same conditions and by the same procedure as in Control Run 1 to obtain 311.2 g of the distillate with an NDCM purity of 99.0% by weight. The amount of the still residue was 42.1 g, and it consisted of 58.4% by weight of NDCM, 18.2% by weight of naphthalenedicarboxylic acid monoester, 5.3% by weight of NDCA, 1.2% by weight of heavy metals (Co= 0.10% by weight, Mn=1.08% by weight), and 16.9% by weight of other high boiling substances.

Then, 300 g of the distillate was recrystallized for purification under the same conditions and by the same procedure as in Control Run 1. The crystals after drying weighted 285.5 g, and gave purified NDCM having an NDCM purity of more than 99.9% by weight.

The yield of NDCM based on the oxidation material (DMN) after all steps, oxidation, esterification and purification, was 83.1 mol %.

TABLE 2

|  | Cont. Run 2 | Ex. 4 |
| --- | --- | --- |
| Content of NDCA composition (wt. %) | 97.1 | 97.8 |
| Yield of NDCA (mol %) | 95.1 | 94.3 |
| Liquid content in cake (wt. %) | 54.2 | 28.8 |
| Average particle diameter (μm) | 16 | 31 |
| Bulk density at sparse packing (g/cm$^3$) | 0.25 | 0.66 |
| Bulk density at dense packing (g/cm$^3$) | 0.41 | 0.87 |
| Degree of compaction (%) | 39 | 24 |
| Angle of repose (degrees) | 65 | 45 |

According to the process of the present invention, the particle diameters of NDCA crystals formed by oxidation can be made large, and their bulk density can also be heightened, thus facilitating solid-liquid separation of the crystals after the reaction, drying of the crystals separated, and the storage and transportation of the powder. Furthermore, the low boiling distillate, the still residue, and the residue of the mother liquor after recrystallization, occurring at the crude NDCM purifying step, are used as additives to the oxidation reaction. Thus, the yield of NDCM in the entire process can be increased, so that NDCA and NDCM can be produced with great commercial advantage.

What is claimed is:

1. A process for producing 2,6-naphthalenedicarboxylic acid, which comprises oxidizing a 2,6-dialkylnaphthalene with a gas containing molecular oxygen in a solvent containing a lower aliphatic carboxylic acid in the presence of a catalyst comprising heavy metal compounds and a bromine compound, wherein an ester mixture containing dimethyl 2,6-naphthalenedicarboxylate is added to the oxidation reaction.

2. A process for producing 2,6-naphthalenedicarboxylic acid as claimed in claim 1, which comprises esterifying 2,6-naphthalenedicarboxylic acid with methanol to produce dimethyl 2,6-naphthalenedicarboxylate, and adding to the oxidation reaction an ester mixture containing dimethyl 2,6-naphthalenedicarboxylate obtained at a step of purifying the dimethyl 2,6-naphthalenedicarboxylate.

3. A process for producing 2,6-naphthalenedicarboxylic acid as claimed in claim 2, wherein the esterification reaction is performed at a temperature of 100° to 320° C. and a pressure of 2 to 200 kg/cm$^2$ G, and at least one of (a) the low boiling distillate obtained during the purification of the reaction product by distillation, (b) the high boiling still residue obtained during the purification of the reaction product by distillation and (c) the residue of the mother liquor obtained during the purification of the reaction product by recrystallization is added to the oxidation reaction.

4. A process for producing dimethyl 2,6-naphthalenedicarboxylate, which comprises oxidizing a 2,6-dialkylnaphthalene with a gas containing molecular oxygen to produce 2,6-naphthalenedicarboxylic acid, and purifying a reaction product obtained by the reaction between the 2,6-naphthalenedicarboxylic acid and methanol, wherein an ester mixture containing dimethyl 2,6-naphthalenedicarboxylate obtained by the purification step is added to the oxidation reaction.

* * * * *